(12) United States Patent
Scheiblich et al.

(10) Patent No.: US 6,534,447 B1
(45) Date of Patent: Mar. 18, 2003

(54) HERBICIDAL PYRIDINE COMPOUNDS

(75) Inventors: Stefan Scheiblich, Mainz (DE); Thomas Maier, Stockach (DE); Helmut Baltruschat, Schweppenhausen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/708,921

(22) Filed: Nov. 8, 2000

Related U.S. Application Data

(60) Provisional application No. 60/165,050, filed on Nov. 12, 1999.

(51) Int. Cl.$^7$ .................. C07D 213/96; C07D 40/12; C07D 409/12; A01N 43/40; A01N 43/56
(52) U.S. Cl. ................ 504/250; 504/251; 504/252; 504/253; 504/256; 546/261; 546/275.4; 546/278.4; 546/280.4; 546/296
(58) Field of Search .................... 504/130, 250, 504/251, 252, 253, 256; 546/261, 275.4, 278.4, 280.4, 296

(56) References Cited

U.S. PATENT DOCUMENTS

| | | | |
|---|---|---|---|
| 4,547,218 A | 10/1985 | Malhotra et al. | 504/253 |
| 5,840,654 A | 11/1998 | Kleemann | 504/251 |
| 6,130,188 A | 10/2000 | Scheiblich et al. | 504/253 |

FOREIGN PATENT DOCUMENTS

| | | |
|---|---|---|
| EP | 0272533 | 6/1988 |
| EP | 955 292 | 11/1999 |
| EP | 955 300 | 11/1999 |
| ZA | 87/09546 | 6/1988 |

OTHER PUBLICATIONS

Paquette, Leo A., Principles of Modern Heterocyclic Chemistry, W.A. Benjamin, New York, 1968, p. 309.*
Streitwieser, A. and Heathcock, C.H., "Introduction to Organic Chemistry, 2nd Ed.", Macmillan, New York, 1981, p. 1105.*

* cited by examiner

Primary Examiner—Mukund J. Shah
Assistant Examiner—Thomas McKenzie
(74) Attorney, Agent, or Firm—Keil & Weinkauf

(57) ABSTRACT

The invention relates to novel compounds of formula I:

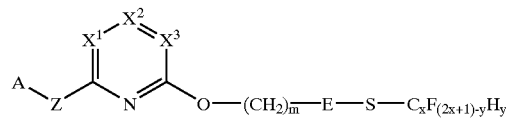

(I)

wherein E, A, $X^1$, $X^2$, $X^3$, Z, m, x and y have the meaning given in claim 1, and the agronomically acceptable salts or N-oxides thereof, and to herbicidal compositions containing such compounds as active ingredients.

6 Claims, No Drawings

HERBICIDAL PYRIDINE COMPOUNDS

This application claims priority from copending provisional application(s) Ser. No. 60/165,050 filed on Nov. 12, 1999.

BACKGROUND OF THE INVENTION

Selective herbicidal compounds play an important role in agriculture and related fields. Growers seek herbicides that kill pest plants, but do not reduce crop yield. Although numerous selective herbicides have been described, there is nevertheless a considerable interest in new compounds having a superior or different activities, because the known herbicidal compounds either are not suitable for application in certain crops, or are not sufficiently selective.

Selective herbicides the active ingredients of which are pyridine derivatives, and particularly 2,6-substituted pyridines, are known from WO 94/22833.

However, 2,6-disubstituted pyridine derivatives in which a fluoroalkylthioalk(en)yloxy group is attached to the pyridine group in the 2-position have not yet been described.

SUMMARY OF THE INVENTION

The present invention provides novel compounds of formula (I)

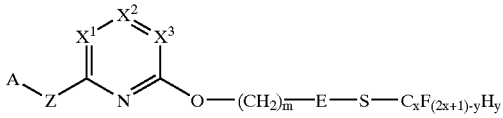

(I)

wherein
- one of the groups $X^1$, $X^2$ and $X^3$ represents N or $CR^1$ and the others represent $CR^1$;
- $R^1$ each independently represent a hydrogen or halogen atom or an optionally substituted alkyl, alkenyl, alkynyl, alkoxy, alkoxyalkyl, alkoxyalkoxy, group or a haloalkyl, haloalkoxy, cyano, nitro or $SF_5$ group; or $-S(O)_p-R^2$, in which p is 0, 1 or 2, and $R^2$ represents an alkyl or haloalkyl group; or $-NR^3R^4$, in which $R^3$ and $R^4$ each independently represent a hydrogen atom, an alkyl, alkenyl, aralkyl or aryl group, or $R^5O-CW-$, in which $R^5$ represents an alkyl group, and W represents O or S;
- A represents an optionally substituted phenyl group, an optionally substituted 5- or 6-membered nitrogen-containing heteroaromatic group or an optionally substituted thienyl group;
- E represents a group selected from the formulae (a) and (b), $$-CH_2CHY- \quad (a)$$

$$-CH=CY- \quad (b)$$

in which Y represents a hydrogen or halogen atom or a cyano or alkyl group;
- Z represents an oxygen or sulfur atom;
- m is 0, 1, 2 or 3;
- x is an integer from 1 to 3; and
- y is 0 or an integer from 1 to 2x;
- and the agronomically acceptable salts or N-oxides thereof.

The new compounds show an excellent selective herbicidal activity in various crops.

It is an object of the present invention to provide novel, selective herbicidal compounds.

It is also an object of the invention to provide methods for controlling undesired plant growth by contacting said plants with a herbicidally effective amount of the new compounds.

It is another object of the invention to provide selective herbicidal compositions containing the new compounds as active ingredients.

These and other objects and features of the invention will be more apparent from the detailed description set forth hereinbelow, and from the appended claims.

DETAILED DESCRIPTION OF THE PREFERRED EMBODIMENTS

It has surprisingly been found that the compounds of the general formula (I)

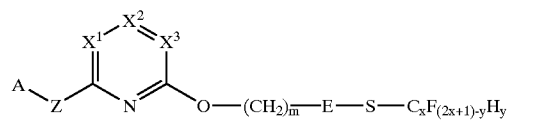

(I)

wherein
A, E, m, x, y $X^1$ through $X^3$ and Z are as described above and the agronomically acceptable salts or N-oxides thereof, show considerable herbicidal activity and high selectivity in certain crops, such as wheat, soybeans, maize and rice, in pre- and post-emergence applications on both broadleaf and grassy weed species.

In the definitions of the new compounds, an aryl group is suitably an optionally substituted phenyl or naphthyl group. Within the definition of A, the 5- or 6-membered nitrogen-containing heteroaryl groups comprise optionally substituted 5- or 6-membered heterocycles containing one or more nitrogen and/or oxygen and/or sulphur atoms, 1 to 3 nitrogen atoms being preferred.

Examples of such groups are pyrazolyl, imidazolyl, triazolyl, tetrazolyl, pyridyl, pyrazinyl, pyrimidyl, pyridazinyl, isoxazolyl, isothiazolyl and triazinyl groups. A also includes optionally substituted thienyl groups.

Generally, in compounds of the present invention, alkyl, alkenyl or alkynyl groups, unless otherwise specified, may be linear or branched and may contain up to 12, preferably up to 6, and most preferably up to 4, carbon atoms. Examples of such groups are methyl, ethyl, propyl, vinyl, allyl, propargyl, isopropyl, butyl, isobutyl and tertiary-butyl groups. The alkyl portion of a haloalkyl, haloalkenyl, haloalkoxy, alkylthio, haloalkylthio or alkoxy group suitably has up to 12 carbon atoms, preferably up to 6, and most preferably up to 4, carbon atoms. The double bond of the alkenyl and haloalkenyl groups is as a rule located in the 1- or 2-position with respect to the point of their attachment. The number of carbon atoms in the alkoxyalkyl, alkoxyalkoxy or dialkoxyalkyl groups is up to 6, preferably up to 4, e.g. methoxymethyl, methoxymethoxy, methoxyethyl, ethoxymethyl, ethoxyethoxy, dimethoxymethyl.

"Halogen" means a fluorine, chlorine, bromine or iodine atom, preferably fluorine, chlorine or bromine.

m is preferably 0, 1 or 2, in particular 1.

Haloalkyl, haloalkenyl, haloalkylthio and haloalkoxy are preferably mono-, di-, tri-, tetra- or pentafluoroalkyl, -alkenyl, -alkylthio and -alkoxy, or monochloro- or dichloroalkenyl, or monobromoalkenyl, especially preferred are trifluoromethyl, tetrafluoroethyl, pentafluoroethyl, octafluorobutyl, 3,3,3-trifluoroprop-1-enyl, 2-methyl-3,3,3-trifluoroprop-1-enyl, 4,4,4-trifluorobut-1-enyl, 1,2-difluorobuta-1,3-dienyl, 1- or 2-chlorovinyl, 2,2-dichlorovinyl, 1,2-dichlorovinyl, 1,2-dichloroprop-1-enyl, 3,3,3-trichloroprop-1-enyl, 2-bromoallyl, difluoromethoxy, trifluoromethylthio, difluoromethylthio and trifluoromethoxy.

When any groups are designated as being optionally substituted, the substituent groups which are optionally present may be any of those customarily employed in the modification and/or development of pesticidal compounds and are especially substituents that maintain or enhance the herbicidal activity associated with the compounds of the present invention, or influence persistence of action, soil or plant penetration, or any other desirable property of such herbicidal compounds.

There may be one or more, preferably one to five, in particular 1, 2 or 3, of the same or different substituents present in each part of the molecules. In relation to moieties defined above as comprising an optionally substituted alkyl group, including alkyl parts of alkenyl, alkynyl, haloalkyl, alkoxy, alkylthio, haloalkoxy, haloalkylthio, alkylamino and dialkylamino groups, specific examples of such substituents include phenyl, halogen atoms, nitro, cyano, hydroxyl, $C_{1-4}$-alkoxy, $C_{1-4}$-haloalkoxy, $C_{1-4}$-haloalkylthio and $C_{1-4}$-alkoxycarbonyl groups.

In relation to moieties defined above as comprising an optionally substituted phenyl or heteroaromatic group, optional substituents include halogen, nitro, cyano, amino, hydroxyl, $C_{1-4}$-alkyl, $C_{1-4}$-alkoxy, $C_{1-4}$-haloalkyl, $C_{1-4}$-haloalkylthio, $C_{1-4}$-haloalkoxy, $C_{2-4}$ haloalkenyl, and halosulfanyl groups having 1–5 halogen atoms, such as $SF_5$. From 1 to 5 substituents may be present, 1 to 2 substituents being preferred. Typically, haloalkyl, haloalkenyl, haloalkoxy and haloalkylthio groups are trifluoromethyl, difluoromethoxy, trifluoromethoxy, difluoromethylthio and trifluoromethylthio groups.

Preferred compounds within the above definitions are those in which A represents a phenyl, pyridyl or pyrazolyl group, unsubstituted or substituted by one or more identical or different substituents selected from halogen atoms, alkyl, alkoxy, haloalkyl, haloalkylthio, haloalkoxy and pentahalosulfanyl groups. Preferably, at least one substituent is attached in the 3-position with respect to the carbon atom attached to the group Z. Most preferred A is a group of formula A,

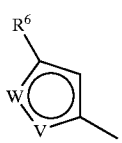

(A)

in which
R$^6$ represents a halogen atom, or an alkyl, alkoxy, haloalkyl, haloalkylthio, haloalkoxy or pentahalosulfanyl group;
W—V represents N—CH, S—CH, N—CH—CH or CH—CH—CH, N—NR$^7$, wherein R$^7$ represents an alkyl group.

X$^1$ and X$^3$ preferably represent CH or C-Halogen, in particular C—F, and X$^2$ represents CR$^1$, in which R$^1$ has the meaning given and is preferably hydogen, cyano, alkyl or alkoxy, in particular $C_{1-4}$alkyl or $C_{1-4}$alkoxy, most preferred methyl, ethyl, methoxy or ethoxy.

x is preferably 1 or 2, in particular 1.
y is preferably 0, 1 or 2, in particular 0.

Accordingly the group —S—$C_xF_{(2x+1)-y}H_y$ preferably represents a trifluoromethylthio, pentafluoroethylthio or 2,2,2-trifluoroethylthio group.

One skilled in the art will appreciate that not all nitrogen containing heterocycles can form N-oxides; one skilled in the art will recognize those nitrogen atoms which can form N-oxides. Synthetic methods for the preparation of N-oxides of heterocycles are very well known by one skilled in the art including the oxidation of heterocycles with peroxy acids such as peracetic acid and m-chloroperbenzoic acid (MCPBA), hydrogen peroxide, alkylhyroperoxides such as tert-butyl hydroperoxide. Such methods for the preparation of N-oxides have been described and reviewed in the literature, as for example: T. L. Gilchrist in Comprehensive Organic Synthesis, vol. 7, pp 748–750 and in Advances in Heterocyclic Chemistry, vol. 9, pp 285–291, vol. 22, pp 390–392 and vol. 43, pp 149–161, A. R. Katritzky. Ed., Academic Press.

Compounds of the invention include compounds of formula I, isotopes thereof, geometric and stereoisomers thereof, N-oxides thereof, and agriculturally suitable salts thereof. The compounds of the invention can exist as one or more stereoisomers. The various isotopes include compounds of formula I, in which at least one natural occurring isotope such as a hydrogen or $^{12}C$ carbon atom is replaced by another isotope thereof such as deuterium or $^{13}C$. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or selectively prepare said stereoisomers. The compounds of the invention may be present as a mixture of stereoisomers, individual stereoisomers, or as an optically active form.

The salts of the compounds of the invention include acid-addition salts of inorganic and organic acids such as hydrobromic, hydrochloric, nitric, phosphoric, sulfuric, acetic, butyric, fumaric, lactic, maleic, oxalic, propionic salicylic, tartaric, toluemnesulfonic or valeric acids.

Preferred embodiments of the present invention are:
(a) A compound of formula I, wherein Z represents an oxygen atom.
(b) A compound of formula I, wherein E represents a group of formula c:

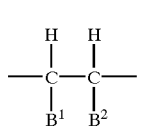

(c)

in which
Y represents a hydrogen or halogen atom; in particular a hydrogen or chloro atom, and B$^1$ and B$^2$ represent a hydrogen or taken together a double bond.
Most preferred are compounds of formula I, wherein $(CH_2)_m$—E— represents a group selected from ethylen-1,2-diyl, propylen-1,3-diyl, 2-chloroethylen-1,2-diyl, prop-2-enylen-1,3-diyl, 3-chloroprop-2-enylen-1,3-diyl and 3-chloropropylen-1,3-diyl.
The double bond of the group —CH=CY— (b) has preferably the (E)-configuration.
(c) A compound of formula I, wherein A represents a group selected from optionally substituted phenyl, pyridyl, thienyl and pyrazolyl, preferably wherein A represents a group selected from the formulae (1), (2), (3), and (4):

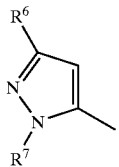
(1)

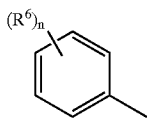
(2)

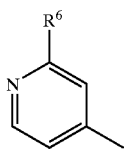
(3)

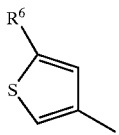
(4)

wherein $R^6$ each independently represents a halogen atom or an optionally substituted alkyl group;

$R^7$ represents an alkyl group; and n represents an integer of 1 to 5, in particular wherein A represents one of the groups 1', 2', 3' or 4':

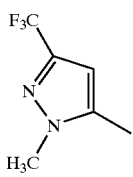
(1')

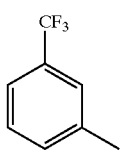
(2')

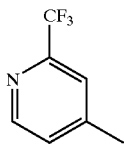
(3')

(4')

(d) A compound of formula IA

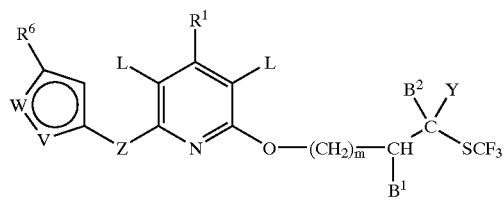
(IA)

wherein $R^1$, $R^6$, $B^1$, $B^2$, Y, m and Z have the meaning given above;

L represents a hydrogen or fluorine atom;

W—V represents N—CH, S—CH, N—CH—CH, CH—CH—CH or N—NCH$_3$.

The compounds of formula IA wherein $B^1$, $B^2$ and Y each represent a hydrogen atom, $R^1$ represents a hydrogen atom or a cyano, methyl or methoxy group and m is 0 or 1 are particularly preferred.

(e) A compound according to claim 1 selected from the group consisting of 2-(1-methyl-3-trifluoromethylpyrazol-5-yloxy)-6-(3-trifluoromethylthio-propoxy)4-methylpyridine; 2-(1-methyl-3-trifluoromethylpyrazol-5-yloxy)-6-(2-trifluoromethylthio-ethoxy)-4-methylpyridine; 2-(1-methyl-3-trifluoromethylpyrazol-5-yloxy)-6-(3-chloro-3-trifluoromethylthiopropoxy)-4-methylpyridine; 2-(5-trifluoromethylthien-3-yloxy)-6-(3-trifluoromethylthiopropoxy)-4-methylpyridine; 2-(5-trifluoromethylthien-3-yloxy)-6-(2-trifluoromethylthioethoxy)-4-methylpyridine; 2-(5-trifluoromethylthien-3-yloxy)-6-(3-chloro-3-trifluoromethylthio-propoxy)-4-methylpyridine; 2-(3-trifluoromethylphenoxy)-6-(3-trifluoromethylthiopropoxy)-4-methylpyridine; 2-(3-trifluoromethylphenoxy)-6-(2-trifluoromethylthioethoxy)-4-methylpyridine; 2-(3-trifluoromethylphenoxy)-6-(3-chloro-3-trifluoromethylthio-propoxy)-4-methylpyridine; 2-(2-difluoromethoxypyrid-4-yloxy)-6-(3-trifluoromethylthiopropoxy)-4-methylpyridine; 2-(2-difluoromethoxypyrid-4-yloxy)-6-(2-trifluoromethylthioethoxy)-4-methylpyridine; 2-(2-difluoromethoxypyrid-4-yloxy)-6-(3-chloro-3-trifluoromethylthio-propoxy)-4-methylpyridine; 2-(2-trifluoromethylpyrid-4-yloxy)-6-(3-trifluoromethylthiopropoxy)-4-methylpyridine; 2-((2-trifluoromethylpyrid-4-yloxy)-6-(2-trifluoromethylthioethoxy)-4-methylpyridine; 2-((2-trifluoromethylpyrid-4-yloxy)-6-(3-chloro-3-trifluoromethylthio-propoxy)-4-methylpyridine; 2-(1-methyl-3-trifluoromethylpyrazol-5-yloxy)-6-(3-trifluoromethylthio-prop-2-enyloxy)-4-methylpyridine; 2-(1-methyl-3-trifluoromethylpyrazol-5-yloxy)-6-(3-chloro-3-trifluoromethylthio-prop-2-enyloxy)-4-methylpyridine; 2-(5-trifluoromethylthien-3-yloxy)-6-(3-trifluoromethylthio-prop-2-enyloxy)-4-methylpyridine; 2-(5-trifluoromethylthien-3-yloxy)-6-(3-chloro-3-trifluoromethylthio-prop-2-enyloxy)-4-methylpyridine; 2-(3-trifluoromethylphenoxy)-6-(3-trifluoromethylthio-prop-2-enyloxy)-4-methylpyridine; 2-(3-trifluoromethylphenoxy)-6-(3-chloro-3-trifluoromethylthio-prop-2-enyloxy)-4-methylpyridine; 2-(2-difluoromethoxypyrid-4-yloxy)-6-(3- trifluoromethylthio-prop-2-enyloxy)-4-methylpyridine; 2-(2-difluoromethoxypyrid-4-yloxy)-6-(3-chloro-3-trifluoromethylthio-prop-2-enyloxy)-4-methylpyridine; 2-(2-trifluoromethylpyrid4-yloxy)-6-(3-trifluoromethylthio-prop-2-enyloxy)-4-methylpyridine; 2-(2-trifluoromethylpyrid4-yloxy)-6-(3-chloro-3-trifluoromethylthio-prop-2-enyloxy)-4-methylpyridine2-(1-methyl-3-trifluoromethylpyrazol-5-yloxy)-6-(3-trifluoromethylthio-propyloxy)-pyridine; 2-(1-methyl-3-trifluoromethylpyrazol-5-yloxy)-6-(2-trifluoromethylthio-ethoxy)-pyridine; 2-(1-methyl-3-trifluoromethylpyrazol-5-yloxy)-6-(3-trifluoromethylthio-propyloxy)-4-cyanopyridine; 2-(1-methyl-3-trifluoromethylpyrazol-5-yloxy)-6-(2-trifluoromethylthio-ethoxy)-4-cyanopyridine; 2-(1-methyl-3-trifluoromethylpyrazol-5-yloxy)-6-(3-trifluoromethylthio-propyloxy)-4-methoxypyridine; 2-(1-methyl-3-trifluoromethylpyrazol-5-yloxy)-6-(2-trifluoromethylthio-ethoxy)-4-methoxypyridine; 2-(3-trifluoromethylphenoxy)-6-(3-trifluoromethylthio-propyloxy)-4-cyanopyridine; 2-(3-trifluoromethylphenoxy)-6-(2-trifluoromethylthio-ethoxy)-4-cyanopyridine; 2-(3-trifluoromethylphenoxy)-6-(3-trifluoromethylthio-propyloxy)-4-methoxypyridine; 2-(3-trifluoromethylphenoxy)-6-(2-trifluoromethylthio-ethoxy)-4-methoxypyridine; 2-(2-difluoromethoxypyrid4-yloxy)-6-(3-trifluoromethylthio-propyloxy)-pyridine; 2-(2-difluoromethoxypyrid4-yloxy)-6-(2-trifluoromethylthio-ethoxy)-pyridine; 2-(2-difluoromethoxypyrid4-yloxy)-6-(3-trifluoromethylthio-propyloxy)-4-cyanopyridine; 2-(2-difluoromethoxypyrid4-yloxy)-6-(2-trifluoromethylthio-ethoxy)-4-cyanopyridine; 2-(2-difluoromethoxypyrid-4-yloxy)-6-(3-trifluoromethylthio-propyloxy)-4-methoxypyridine; 2-(2-difluoromethoxypyrid-4-yloxy)-6-(2-trifluoromethylthio-ethoxy)-4-methoxypyridine; 2-(2-trifluoromethylpyrid-4-yloxy)-6-(3-trifluoromethylthio-propyloxy)-pyridine; 2-(2-trifluoromethylpyrid-4-yloxy)-6-(2-trifluoromethylthio-ethoxy)-pyridine; 2-(2-trifluoromethylpyrid-4-yloxy)-6-(3-trifluoromethylthio-propyloxy)-4-cyanopyridine; 2-(2-trifluoromethylpyrid-4-yloxy)-6-(2-trifluoromethylthio-ethoxy)-4-cyanopyridine; 2-(2-trifluoromethylpyrid-4-yloxy)-6-(3-trifluoromethylthio-propyloxy)-4-methoxypyridine; 2-(2-trifluoromethylpyrid-4-yloxy)-6-(2-trifluoromethylthio-ethoxy)-4-methoxypyridine.

The compounds of this invention can be prepared according to known methods, particularly with the aid of the following methods:

Method (B): Reacting a respective compound of formula II, $$\underset{A}{\overset{X^1}{\diagdown}}\underset{Z}{\overset{X^2}{\diagdown}}\underset{N}{\overset{X^3}{\diagdown}}\underset{O}{\diagdown}B \qquad (II)$$

in which A, $X^1$, $X^2$, $X^3$ and Z have the meaning given, and B represents a group A, with a compound of general formula III, $$HO-(CH_2)_m-E-S-C_xF_{(2x+1)-y}H_y \qquad (III)$$

in which E, m, x and y have the meaning given, or a metal salt thereof.

Method (B): Alternatively, a compound of formula II, in which A, Z and $X^1$ through $X^3$ have the meaning given, and B represents a hydrogen atom, is reacted with a compound of formula III in the presence of a dehydrating agent, preferably in the presence of triphenylphosphine and diethyl azodicarboxylate (Mitsunobu method).

Method (C): Alternatively, a compound of formula II, in which A, Z and $X^1$ through $X^3$ have the meaning given, and B represents a hydrogen atom, is reacted with a compound of formula IV, $$LG^1-(CH_2)_m-E-S-C_xF_{(2x+1)-y}H_y \qquad (IV)$$

in which $LG^1$ represents a suitable leaving group, such as a halogen atom or a tosylate or mesylate group, in the presence of a base.

Method (D): Alternatively, a compound of formula V, $$\underset{LG^2}{\overset{X^1}{\diagdown}}\underset{N}{\overset{X^2}{\diagdown}}\underset{}{\overset{X^3}{\diagdown}}O-(CH_2)_{\overline{m}}-E-S-C_xF_{(2x+1)-y}H_y \qquad (V)$$

wherein E, $X^1$, $X^2$, $X^3$, m, x and y have the meaning given for formula I, and $LG^2$ denotes a suitable leaving group, is reacted with a compound of formula VI, $$A-ZH \qquad (VI)$$

in which A and Z have the meaning given, in the presence of a base.

These reactions are conveniently carried out in an organic solvent at elevated temperature. Generally, any polar organic solvent is suitable, e.g. dimethylformamide, N-mehylpyrrolidone, tetrahydrofuran, sulfolane, pyridines. The metal salts of the compounds of formula III are suitably alkali metal salts, preferably the sodium or potassium salts. In some cases, the presence of copper salts has been found to be useful.

The metal salts are conveniently generated by reaction of the compound of formula III with a suitable metal base, a metal carbonate or hydride.

The prepared compounds of formula I may be isolated and purified using conventional methods and techniques.

The starting compounds for the preparation of compounds of this invention are either known from WO 94/22833 or can be prepared according to known methods.

The intermediates of formulae III and IV are partly known and partly novel. Therefore, the application relates to the novel compounds of formula III and IV, in particular to the compounds of formula IIIa $$LG^3-CH_2-E-S-CF_3 \qquad (IIIa)$$

in which
$LG^3$ represents a halogen atom or a hydroxy, tosylate or mesylate group;
E represents a group selected from $-CH_2CH_2-$, $-CH=CH-$ and $-CH=CCl-$.

The intermediates of formula III may be obtained by reaction of the corresponding thiols of formula VII $$HO-(CH_2)_m-E-S-H \qquad (VII)$$

wherein E and m have the meaning given for formula III, with the corresponding fluoroalkyliodides of formula VIII $$I-C_xF_{(2x+1)-y}H_y \qquad (VIII)$$

wherein x and y have the meaning given for formula III, in the presence of a base and optionally under irradiation with UV light.

The compounds of formula IV may be prepared from the compounds of formula III by conventional derivatization techniques as for example reaction with halogenation agents or with mesylchloride or toyslchloride. Alternatively, the compounds of formula IV, wherein m is 1, LG1 is bromo and E is —CH═CH—, may also be obtained by reaction of 1-trifluoromethylthiopro-2-ene with a bromination agent, as for example N-bromo-succinimide (NBS).

The compounds of general formula I have been found to have herbicidal activity. Accordingly, the invention further provides a herbicidal composition which comprises an active ingredient, which is at least one compound of formula I as defined above, and one or more carriers. A method of making such a composition is also provided which comprises bringing a compound of formula I as defined above into association with the carrier(s). Such a composition may contain a single active ingredient or a mixture of several active ingredients of the present invention. It is also envisaged that different isomers or mixtures of isomers may have different levels or spectra of activity and thus compositions may comprise individual isomers or mixtures of isomers.

A composition according to the invention preferably contains from 0.5% to 95% by weight (w/w) of active ingredient.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including material which is normally a gas but which has been compressed to form a liquid.

The compositions may be manufactured into e.g. emulsion concentrates, solutions, oil in water emulsions, wettable powders, soluble powders, suspension concentrates, dusts, granules, water dispersible granules, micro-capsules, gels and other formulation types by well-established procedures. These procedures include intensive mixing and/or milling of the active ingredients with other substances, such as fillers, solvents, solid carriers, surface active compounds (surfactants), and optionally solid and/or liquid auxilaries and/or adjuvants. The form of application such as spraying, atomizing, dispersing or pouring may be chosen like the compositions according to the desired objectives and the given circumstances.

Solvents may be aromatic hydrocarbons, e.g. Solvesso® 200, substituted naphthalenes, phthalic acid esters, such as dibutyl or dioctyl phthalate, aliphatic hydrocarbons, e.g. cyclohexane or paraffins, alcohols and glycols as well as their ethers and esters, e.g. ethanol, ethyleneglycol mono- and dimethyl ether, ketones such as cyclohexanone, strongly polar solvents such as N-methyl-2-pyrrolidone, or γ-butyrolactone, higher alkyl pyrrolidones, e.g. n-octylpyrrolidone or cyclohexylpyrrolidone, epoxidized plant oil esters, e.g. methylated coconut or soybean oil ester and water. Mixtures of different liquids are often suitable.

Solid carriers, which may be used for dusts, wettable powders, water dispersible granules, or granules, may be mineral fillers, such as calcite, talc, kaolin, montmorillonite or attapulgite. The physical properties may be improved by addition of highly dispersed silica gel or polymers. Carriers for granules may be porous material, e.g. pumice, kaolin, sepiolite, bentonite; non-sorptive carriers may be calcite or sand. Additionally, a multitude of pre-granulated inorganic or organic materials may be used, such as dolomite or crushed plant residues.

Pesticidal compositions are often formulated and transported in a concentrated form which is subsequently diluted by the user before application. The presence of small amounts of a carrier which is a surfactant facilitates this process of dilution. Thus, preferably at least one carrier in a composition according to the invention is a surfactant. For example, the composition may contain at two or more carriers, at least one of which is a surfactant.

Surfactants may be nonionic, anionic, cationic or zwitterionic substances with good dispersing, emulsifying and wetting properties depending on the nature of the compound according to general formula I to be formulated. Surfactants may also mean mixtures of individual surfactants.

The compositions of the invention may for example be formulated as wettable powders, water dispersible granules, dusts, granules, solutions, emulsifiable concentrates, emulsions, suspension concentrates and aerosols. Wettable powders usually contain 5 to 90% w/w of active ingredient and usually contain in addition to solid inert carrier, 3 to 10% w/w of dispersing and wetting agents and, where necessary, 0 to 10% w/w of stabilizer(s) and/or other additives such as penetrants or stickers. Dusts are usually formulated as a dust concentrate having a similar composition to that of a wettable powder but without a dispersant, and may be diluted in the field with further solid carrier to give a composition usually containing 0.5 to 10% w/w of active ingredient. Water dispersible granules and granules are usually prepared to have a size between 0.15 mm and 2.0 mm and may be manufactured by a variety of techniques. Generally, these types of granules will contain 0.5 to 90% w/w active ingredient and 0 to 20% w/w of additives such as stabilizer, surfactants, slow release modifiers and binding agents. The so-called "dry flowables" consist of relatively small granules having a relatively high concentration of active ingredient. Emulsifiable concentrates usually contain, in addition to a solvent or a mixture of solvents, 1 to 80% w/v active ingredient, 2 to 20% w/v emulsifiers and 0 to 20% w/v of other additives such as stabilizers, penetrants and corrosion inhibitors. Suspension concentrates are usually milled so as to obtain a stable, non-sedimenting flowable product and usually contain 5 to 75% w/v active ingredient, 0.5 to 15% w/v of dispersing agents, 0.1 to 10% w/v of suspending agents such as protective colloids and thixotropic agents, 0 to 10% w/v of other additives such as defoamers, corrosion inhibitors, stabilizers, penetrants and stickers, and water or an organic liquid in which the active ingredient is substantially insoluble; certain organic solids or inorganic salts may be present dissolved in the formulation to assist in preventing sedimentation and crystalization or as antifreeze agents for water.

Aqueous dispersions and emulsions, for example compositions obtained by diluting the formulated product according to the invention with water, also lie within the scope of the invention.

Of particular interest in enhancing the duration of the protective activity of the compounds of this invention is the use of a carrier which will provide slow release of the pesticidal compounds into the environment of a plant which is to be protected.

The biological activity of the active ingredient can also be increased by including an adjuvant in the spray dilution. An adjuvant is defined here as a substance which can increase the biological activity of an active ingredient but is not itself significantly biologically active. The adjuvant can either be included in the formulation as a coformulant or carrier, or can be added to the spray tank together with the formulation containing the active ingredient.

As a commodity the compositions may preferably be in a concentrated form whereas the end user generally employs diluted compositions. The compositions may be diluted to a concentration down to 0.001% of active ingredient. The doses usually are in the range from 0.01 to 10 kg a.i./ha.

Examples of formulations according to the invention are:

| Emulsion Concentrate (EC) | | |
|---|---|---|
| Active Ingredient | Compound of Example 3 | 30% (w/v) |
| Emulsifier(s) | e.g. Atlox ® 4856 B and Atlox ® 4857 B[1)] | 5% (w/v) |
| Solvent | e.g. Shellsol ® A[2)] | to 1000 ml |
| Suspension Concentrate (SC) | | |
| Active Ingredient | Compound of Example 3 | 50% (w/v) |
| Dispersing agent | e.g. Soprophor ® FL[3)] | 3% (w/v) |
| Antifoaming agent | e.g. Rhodorsil ® 422[3)] | 0.2% (w/v) |
| Structure agent | e.g. Kelzan ® S[4)] | 0.2% (w/v) |
| Antifreezing agent | e.g. Propylene glycol | 5% (w/v) |
| Biocidal agent | e.g. Proxel ®[5)] | 0.1% (w/v) |
| Water | | to 1000 ml |
| Wettable Powder (WP) | | |
| Active Ingredient | Compound of Example 3 | 60% (w/w) |
| Wetting agent | e.g. Atlox ® 4995[1)] | 2% (w/w) |
| Dispersing agent | e.g. Witcosperse ® D-60[6)] | 3% (w/w) |
| Carrier/Filler | e.g. Kaolin | 35% (w/w) |
| Water Dispersible Granules | | |
| Active Ingredient | Compound of Example 3 | 50% (w/w) |
| Dispersing/Binding agent | e.g. Witcosperse ® D-450[6)] | 8% (w/w) |
| Wetting agent | e.g. Morwet ® EFW[6)] | 2% (w/w) |
| Antifoaming agent | e.g. Rhodorsil ® EP 6703[3)] | 1% (w/w) |
| Disintegrant | e.g. Agrimer ® ATF[7)] | 2% (w/w) |
| Carrier/Filler | e.g. Kaolin | 35% (w/w) |

[1)]Product commercially available from ICI Surfactants
[2)]Product commercially available from Deutsche Shell AG
[3)]Product commercially available from Rhône-Poulenc
[4)]Product commercially available from Kelco Co.
[5)]Product commercially available from Zeneca
[6)]Product commercially available from Witco
[7)]Product commercially available from International Speciality Products The compositions of this invention can also comprise other compounds having biological activity, e.g. compounds having similar or complementary pesticidal activity or compounds having plant growth regulating, fungicidal/herbicidal or insecticidal activity. These mixtures of pesticides can have a broader spectrum of activity than the compound of general formula I alone. Furthermore, the other pesticide can have a synergistic effect on the pesticidal activity of the compound of general formula I.

The active ingredients according to the invention can be employed alone or as formulations in combination with conventional herbicides. Such combinations of at least two herbicides can be included in the formulation or also added in a suitable form with the preparation of the tank mix. For such mixtures at least one of the following known herbicides can be used:

ametrydione, metabenzthiazuron, metamitron, metribuzin, 2,4-D, 2,4-DB, 2,4-DP, alachlor, alloxydim, asulam, atrazin, bensulfuron, bentazon, bifenox, bromoxynil, butachlor, carfentrazone, chloridazon, chlorimuron, chlorpropham, chlorsulfuron, chlortoluron, cinmethylin, clopyralid, cyanazin, cycloate, cycloxydim, dichlobenil, diclofop, eptame, ethiozin, fenoxaprop, fluazifop, fluometuron, flupyrsulfuron, fluridone, fluroxypyr, fomesafen, glyphosate, haloxyfop, hexazinone, imazamethabenz, imazapyr, imazaquin, imazethapyr, ioxynil, isoproturon, lactofen, MCPA, MCPP, mefenacet, metazachlor, metolachlor, metsulfuron, molinate, norflurazon, oryzalin, oxyfluorfen, pendimethalin, picloram, pretilachlor, propachlor, pyridate, quizalofopethyl, sethoxydim, simetryne, terbutryne, thiobencarb, triallate, trifluralin, diflufenican, propanil, triclopyr, dicamba, desmedipham, acetochlor, fluoroglycofen, halosafen, tralkoxydim, amidosulfuron, cinosulfuron, nicosulfuron, pyrazosulfuron, thiameturon, thifensulfuron, triasulfuron, oxasulfuron, azimsulfuron, tribenuron, esprocarb, prosulfocarb, terbutylazin, benfuresate, clomazone, di-methazone, dithiopyr, isoxaben, quinchlorac, qinmerac, sulfosate, cyclosulfamuron, imazamox, imazamethapyr, flamprop-M-methyl, flamprop-M-isopropyl, picolinafen, thiafluamide, isoxaflutole, flurtamone, daimuron, bromobutide, methyidimron, dimethenamid, sulcotrione, sulfentrazone, oxadiargyl, aciflurofen, cafenstrole, carfentrazone, diuron, glufosinate.

Mixtures with other active ingredients like fungicides, insecticides, acaricides, and nematicides are possible.

For a more clear understanding of the invention, specific examples are set forth below. These examples are merely illustrations and are not to be understood as limiting the scope and underlying principles of the invention in any way. Various modifications of the invention in addition to those shown and described herein will become apparent to those skilled in the art from the following examples and foregoing description. Such modifications are also intended to fall within the scope of the appended claims.

Preparation of Intermediates

EXAMPLE A

Preparation of 2-(trifluoromethylthio)-ethanol

Iodotrifluoromethane (39.2 g) is added to a mixture of 7.8 g 2-mercaptoethanol and 50 ml of ammoniak at −70° C. The resulting mixture is stirred under irradiation with a Hg lamp at −35° C. for 2 hours. Subsequently, the reaction is allowed to warm to ambient temperature and stirred for 20 hours without irradiation. A dilute sodium hydroxide solution is added and the residue is extracted with ether. The organic phase is separated, dried and concentrated to obtain 12.65 g of 2-(trifluoromethylthio)-ethanol, which can be used without further purification. Analogously are obtained: 3-(trifluoromethylthio)-propanol 4-(trifluoromethylthio)-butanol

EXAMPLE B

Preparation of 1-bromo-3-(trifluoromethylthio)-prop-2-ene
B1 1-(Trifluoromethylthio)-prop-2-ene Liquid iodotrifluoromethane (39.2 g) is added to a mixture of 9.25 g allylmercaptan and 50 ml of ammoniak at −70° C. The resulting mixture is stirred under irradiation with a Hg lamp at −30° C. for 2 hours. Subsequently, the reaction is allowed to warm to ambient temperature and stirred for 20 hours without irradiation. A dilute sodium hydroxide solution is added and the residue is extracted with ether. The organic phase is separated, dried and concentrated The residue is distilled to obtain 1.6 g of 1-(trifluoromethylthio)-prop-2-ene.
B2 1-Bromo-3-(trifluoromethylthio)-prop-2-ene A trace of azoisobutyronitrile is added to a mixture of 0.85 g B1, 1.19 g NBS and 15 ml tetrachloromethane. The mixture is stirred under reflux for 5 hours. Subsequently, the mixture is cooled to ambient temperature, filtered and concentrated to obtain 1.05 g of crude 1-bromo-3-(trifluoromethylthio)-prop-2-ene, which can be used without further purification.

EXAMPLE C

Preparation of 1-hydroxy-3-(2,2,2-trifluoroethylthio)-prop-2-ene

A mixture of 2.32 g 2,2,2-trifluoroethanethiol, 1.12 prop-2-yne-1-ol, 300 mg potassium hydroxide and 40 ml dimethylformamide is stirred at ambient temperature for 20 hours. The mixture is poured into 150 ml of water and extracted with 100 ml ethyl acetate (3 times). The organic phase is washed with water, dried and concentrated. The crude product is purified by column chromatography to obtain 75 mg of pure 1-hydroxy-3-(2,2,2-trifluoroethylthio)-prop-2-ene.

EXAMPLE 1

Preparation of 2-(1-methyl-3-trifluoromethylpyrazol-5-yloxy)-6-(2-trifluoromethylthioethoxy)-4-methylpyridine 1A 6-Hydroxy-2-(1-methyl-3-trifluoromethylpyrazol-5-yloxy)-4-methylpyridine A mixture of 2,6-bis(1-methyl-3-trifluoromethylpyrazol-5-yloxy)-4-methylpyridine (prepared according to WO 94/22833; 4.2 g, 10 mmol) and NaOH (1 g, 25 mmol) is heated in DMSO (50 ml) and water (5 ml) for 36 h at 100° C. After cooling, the reaction mixture is diluted with water and acidified with hydrochloric acid. The mixture is diluted with pentane/ethyl acetate (300 ml by volume ration 1/1) and the organic layer is washed 6 times with water. The organic layer is dried with anhydrous magnesium sulfate, filtered and evaporated in vacuo. Purification by flash chromatography (silica gel: pentane/ethyl acetate 8/2 v/v and 7/3 v/v) yields the title compound (1.9 g, 70% yield) of m.p. 159° C.

1B 2-(1-methyl-3-trifluoromethylpyrazol-5-yloxy)-6-(2-trifluoromethylthioethoxy)-4-methylpyridine A mixture of 1A (0.55 g), 2-(trifluoromethylthio)-ethanol (0.35 g, Example A), triphenylphosphine (0.64 g) and diethyl azodicarboxylate (0.42 g) in dry tetrahydrofuran (5 ml) is stirred for 20 hours at ambient temperature. The reaction mixture is diluted with pentane/ethyl acetate (by volume ration 1/1) and filtered through a bed of silica gel. The filtrate is washed with water. The organic layer is dried with anhydrous magnesium sulfate, filtered and evaporated in vacuo. Purification by flash chromatography (silica gel: pentane/ethyl acetate 9/1 v/v) yields 0.45 g of the title compound as an colorless oil.

EXAMPLE 2

2-(1-Methyl-3-trifluoromethylpyrazol-5-yloxy)-4-methyl-6-(3-trifluoromethylthioprop-2-enyloxy)pyridine 1-Bromo-3-(trifluoromethylthio)-prop-2-ene (1.05 g, Example B) is added to a mixture of 1A (1.08 g), sodium hydride (60% in oil, 0.18 g) and N-methylpyrrolidone (20 ml) and DMF (1 ml). The reaction mixture is stirred for 6 hours at 120° C. The remaining sodium hydride is deactivated and the resulting mixture is diluted with pentane/ethyl acetate (by volume ration 1/1) and filtered through a bed of silica gel. The filtrate is washed with water. The organic layer is dried with anhydrous magnesium sulfate, filtered and evaporated in vacuo. Purification by flash chromatography (silica gel: pentane/ethyl acetate 10/1 v/v) yields 0.3 g of the title compound.

EXAMPLE 3

2-(1-Methyl-3-trifluoromethylpyrazol-5-yloxy)-4-methyl-6-(3-chloro-3-trifluoromethylthiopropyloxy)pyridine 16.2 g sulfurylchloride are added to mixture of 0.8 g 3-(trifluoromethylthio)-propanol (obtained in analogy to example A) and 20 ml tetrachloromethane. The mixture is stirred under reflux for 3 hours. Subsequently, azoisobutyronitrile is added and the mixture is stirred under reflux for additional 9 hours. The mixture is concentrated, diluted with dichloromethane, filtered and concentrated. The obtained residue (1.6 g) is added to a mixture of 1A (3.4 g), sodium hydride (60% in oil, 0.5 g) and DMF (25 ml). The reaction mixture is stirred for 12 hours at ambient temperature. The remaining sodium hydride is deactivated and the resulting mixture is diluted with pentane/ethyl acetate (by volume ration 6/1) and filtered through a bed of silica gel. The filtrate dried with anhydrous magnesium sulfate, filtered and evaporated in vacuo. The title compound (0.1 g) is isolated from the residue which additionally contains the corresponding 6-(3-chloro-3-trifluoromethylthioprop-2-enyloxy)-compound (example 4) by preparative HPLC chromatography (water/acetonitrile).

EXAMPLES 4–82

The compounds listed in TABLE 1 can be prepared by methods analogeous to those described in examples 1 to 3, and according to the methods described in the foregoing description.

TABLE 1

Compounds of formula Ia (Ia)

A—O—[pyridine ring with $R^1$, $Y^1$, $Y^2$ substituents]—O—(CH$_2$)$_m$—E—SCF$_3$

| Example | A | $Y^1$ | $R^1$ | $Y^2$ | m | -E- |
|---|---|---|---|---|---|---|
| 4 | 1-CH$_3$-3-CF$_3$-pyrazol-5-yl | H | CH$_3$ | H | 1 | —CH$_2$CH$_2$— |
| 5 | 1-CH$_3$-3-CF$_3$-pyrazol-5-yl | H | CH$_3$ | H | 1 | —CH=CCl— |
| 6 | 1-CH$_3$-3-CF$_3$-pyrazol-5-yl | F | CH$_3$ | F | 0 | —CH$_2$CH$_2$— |
| 7 | 1-CH$_3$-3-CF$_3$-pyrazol-5-yl | F | CH$_3$ | F | 1 | —CH$_2$CH$_2$— |
| 8 | 1-CH$_3$-3-CF$_3$-pyrazol-5-yl | F | CH$_3$ | F | 1 | —CH$_2$CHCl— |
| 9 | 1-CH$_3$-3-CF$_3$-pyrazol-5-yl | F | CH$_3$ | F | 1 | —CH=CCl— |
| 10 | 1-CH$_3$-3-CF$_3$-pyrazol-5-yl | F | CH$_3$ | F | 1 | —CH=CH— |
| 11 | 3-CF$_3$-phenyl | H | CH$_3$ | H | 0 | —CH$_2$CH$_2$— |
| 12 | 3-CF$_3$-phenyl | H | CH$_3$ | H | 1 | —CH=CH— |
| 13 | 3-CF$_3$-phenyl | H | CH$_3$ | H | 1 | —CH$_2$CH$_2$— |
| 14 | 3-CF$_3$-phenyl | H | CH$_3$ | H | 1 | —CH$_2$CHCl— |
| 15 | 3-CF$_3$-phenyl | H | CH$_3$ | H | 1 | —CH=CCl— |

TABLE 1-continued

Compounds of formula Ia (Ia)

$$\text{A}-\text{O}-\underset{\underset{N}{\|}}{\overset{Y^1\underset{R^1}{\diagup}\diagdown Y^2}{\diagup\diagdown}}-\text{O}-(\text{CH}_2)_m-\text{E}-\text{SCF}_3$$

| Example | A | Y¹ | R¹ | Y² | m | -E- |
|---------|---|----|----|----|---|-----|
| 16 | 3-CF₃-phenyl | F | CH₃ | F | 0 | —CH₂CH₂— |
| 17 | 3-CF₃-phenyl | F | CH₃ | F | 1 | —CH₂CH₂— |
| 18 | 3-CF₃-phenyl | F | CH₃ | F | 1 | —CH₂CHCl— |
| 19 | 3-CF₃-phenyl | F | CH₃ | F | 1 | —CH=CCl— |
| 20 | 3-CF₃-phenyl | F | CH₃ | F | 1 | —CH=CH— |
| 21 | 5-CF₃-thien-3-yl | H | CH₃ | H | 0 | —CH₂CH₂— |
| 22 | 5-CF₃-thien-3-yl | H | CH₃ | H | 1 | —CH=CH— |
| 23 | 5-CF₃-thien-3-yl | H | CH₃ | H | 1 | —CH₂CH₂— |
| 24 | 5-CF₃-thien-3-yl | H | CH₃ | H | 1 | —CH₂CHCl— |
| 25 | 5-CF₃-thien-3-yl | H | CH₃ | H | 1 | —CH=CCl— |
| 26 | 5-CF₃-thien-3-yl | F | CH₃ | F | 0 | —CH₂CH₂— |
| 27 | 5-CF₃-thien-3-yl | F | CH₃ | F | 1 | —CH₂CH₂— |
| 28 | 5-CF₃-thien-3-yl | F | CH₃ | F | 1 | —CH₂CHCl— |
| 29 | 5-CF₃-thien-3-yl | F | CH₃ | F | 1 | —CH=CCl— |
| 30 | 5-CF₃-thien-3-yl | F | CH₃ | F | 1 | —CH=CH— |
| 31 | 2-chloropyrid-4-yl | H | CH₃ | H | 0 | —CH₂CH₂— |
| 32 | 2-chloropyrid-4-yl | H | CH₃ | H | 1 | —CH=CH— |
| 33 | 2-chloropyrid-4-yl | H | CH₃ | H | 1 | —CH₂CH₂— |
| 34 | 2-chloropyrid-4-yl | H | CH₃ | H | 1 | —CH₂CHCl— |
| 35 | 2-chloropyrid-4-yl | H | CH₃ | H | 1 | —CH=CCl— |
| 36 | 2-chloropyrid-4-yl | F | CH₃ | F | 0 | —CH₂CH₂— |
| 37 | 2-chloropyrid-4-yl | F | CH₃ | F | 1 | —CH₂CH₂— |
| 38 | 2-chloropyrid-4-yl | F | CH₃ | F | 1 | —CH₂CHCl— |
| 39 | 2-chloropyrid-4-yl | F | CH₃ | F | 1 | —CH=CCl— |
| 40 | 2-chloropyrid-4-yl | F | CH₃ | F | 1 | —CH=CH— |
| 41 | 2-difluoromethoxypyrid-4-yl | H | CH₃ | H | 0 | —CH₂CH₂— |
| 42 | 2-difluoromethoxypyrid-4-yl | H | CH₃ | H | 1 | —CH=CH— |
| 43 | 2-difluoromethoxypyrid-4-yl | H | CH₃ | H | 1 | —CH₂CH₂— |
| 44 | 2-difluoromethoxypyrid-4-yl | H | CH₃ | H | 1 | —CH₂CHCl— |
| 45 | 2-difluoromethoxypyrid-4-yl | H | CH₃ | H | 1 | —CH=CCl— |
| 46 | 2-difluoromethoxypynd-4-yl | F | CH₃ | F | 0 | —CH₂CH₂— |
| 47 | 2-difluoromethoxypynd-4-yl | F | CH₃ | F | 1 | —CH₂CH₂— |
| 48 | 2-difluoromethoxypyrid-4-yl | F | CH₃ | F | 1 | —CH₂CHCl— |
| 49 | 2-difluoromethoxypyrid-4-yl | F | CH₃ | F | 1 | —CH=CCl— |
| 50 | 2-difluoromethoxypyrid-4-yl | F | CH₃ | F | 1 | —CH=CH— |
| 51 | 2-trifluoromethylpyrid-4-yl | H | CH₃ | H | 0 | —CH₂CH₂— |
| 52 | 2-trifluoromethylpyrid-4-yl | H | CH₃ | H | 1 | —CH=CH— |
| 53 | 2-trifluoromethylpyrid-4-yl | H | CH₃ | H | 1 | —CH₂CH₂— |
| 54 | 2-trifluoromethylpyrid-4-yl | H | CH₃ | H | 1 | —CH₂CHCl— |
| 55 | 2-trifluoromethylpyrid-4-yl | H | CH₃ | H | 1 | —CH=CCl— |
| 56 | 2-trifluoromethylpyrid-4-yl | F | CH₃ | F | 0 | —CH₂CH₂— |
| 57 | 2-trifluoromethylpyrid-4-yl | F | CH₃ | F | 1 | —CH₂CH₂— |
| 58 | 2-trifluoromethylpyrid-4-yl | F | CH₃ | F | 1 | —CH₂CHCl— |
| 59 | 2-trifluoromethylpyrid-4-yl | F | CH₃ | F | 1 | —CH=CCl— |
| 60 | 2-trifluoromethylpyrid-4-yl | F | CH₃ | F | 1 | —CH=CH— |
| 61 | 1-CH₃-3-CF₃-pyrazol-5-yl | H | H | H | 1 | —CH₂CH₂— |
| 62 | 1-CH₃-3-CF₃-pyrazol-5-yl | H | H | H | 0 | —CH₂CH₂— |
| 63 | 1-CH₃-3-CF₃-pyrazol-5-yl | H | CN | H | 1 | —CH₂CH₂— |
| 64 | 1-CH₃-3-CF₃-pyrazol-5-yl | H | CN | H | 0 | —CH₂CH₂— |
| 65 | 1-CH₃-3-CF₃-pyrazol-5-yl | H | OCH₃ | H | 1 | —CH₂CH₂— |
| 66 | 1-CH₃-3-CF₃-pyrazol-5-yl | H | OCH₃ | H | 0 | —CH₂CH₂— |
| 67 | 3-CF₃-phenyl | H | CN | H | 1 | —CH₂CH₂— |
| 68 | 3-CF₃-phenyl | H | CN | H | 0 | —CH₂CH₂— |
| 69 | 3-CF₃-phenyl | H | OCH₃ | H | 1 | —CH₂CH₂— |
| 70 | 3-CF₃-phenyl | H | OCH₃ | H | 0 | —CH₂CH₂— |
| 71 | 2-difluoromethoxypyrid-4-yl | H | H | H | 1 | —CH₂CH₂— |
| 72 | 2-difluoromethoxypyrid-4-yl | H | H | H | 0 | —CH₂CH₂— |
| 73 | 2-difluoromethoxypyrid-4-yl | H | CN | H | 1 | —CH₂CH₂— |
| 74 | 2-difluoromethoxypyrid-4-yl | H | CN | H | 0 | —CH₂CH₂— |
| 75 | 2-difluoromethoxypyrid-4-yl | H | OCH₃ | H | 1 | —CH₂CH₂— |
| 76 | 2-difluoromethoxypyrid-4-yl | H | OCH₃ | H | 0 | —CH₂CH₂— |
| 77 | 2-trifluoromethylpyrid-4-yl | H | H | H | 1 | —CH₂CH₂— |
| 78 | 2-trifluoromethylpyrid-4-yl | H | H | H | 0 | —CH₂CH₂— |
| 79 | 2-trifluoromethylpyrid-4-yl | H | CN | H | 1 | —CH₂CH₂— |
| 80 | 2-trifluoromethylpyrid-4-yl | H | CN | H | 0 | —CH₂CH₂— |

TABLE 1-continued

Compounds of formula Ia (Ia)

$$\text{A}-\text{O}-\underset{\underset{N}{\bigcirc}}{\overset{Y^1 \quad R^1 \quad Y^2}{\bigcirc}}-\text{O}-(CH_2)_m-E-SCF_3$$

| Example | A | $Y^1$ | $R^1$ | $Y^2$ | m | -E- |
|---|---|---|---|---|---|---|
| 81 | 2-trifluoromethylpyrid-4-yl | H | $OCH_3$ | H | 1 | —$CH_2CH_2$— |
| 82 | 2-trifluoromethylpyrid-4-yl | H | $OCH_3$ | H | 0 | —$CH_2CH_2$— |

Herbicidal Activity Tests

1. Pre-emergence Herbicidal Evaluation of Test Compounds

The pre-emergence herbicidal activity of the compounds of the present invention is exemplified by the following test in which the seeds of a variety of monocotyledonous and dicotyledonous plants are seperately mixed with potting soil and planted on top of approximately one inch of soil in separate post. After planting, the pots are sprayed with the selected aqueous acetone solution. containing test compound in sufficient quantity to provide the equivalent of about 0.025 to 0.4 kg per hectare of test compound per pot. The treated pots are then placed on greenhouse benches, watered and cared for in accordance with conventional greenhouse procedures. From 3 weeks after treatment, the tests are terminated and each pot is examined and rated according to the rating system set forth below.

| Rating System | % Difference in Growth Versus Untreated Control |
|---|---|
| 0 - No effect | 0 |
| 1 - Trace effect | 1–5 |
| 2 - Slight effect | 6–15 |
| 3 - Moderate effect | 16–29 |
| 4 - Injury | 30–44 |
| 5 - Definite injury | 45–64 |
| 6 - Herbicidal effect | 65–79 |
| 7 - Good herbicidal effect | 80–90 |
| 8 - Approaching complete kill | 91–99 |
| 9 - Complete kill | 100 |

| Plant Species Used | | |
|---|---|---|
| GLXMA | Glycine max | soyabeans |
| TRZAW | Triticum aestivum | winter wheat |
| ZEAMX | Zea mays | maize |
| ABUTH | Abutilon theophrasti | velvetleaf |
| GALAP | Galium aparine | cleaver |
| IPOHE | Ipomoea hederacea | morning glory |
| LOLMU | Dolium multiflorum | ryegrass |
| MATIN | Matricaria inodora | mayweed |
| STEME | Stellaria media | chickweed |
| ALOMY | Alopecurus myosuroides | black grass |
| ECHCG | Echinochloa grus galli | barnyard grass |
| SETVI | Setaria viridis | green foxtail |

The herbicidal proficiency of the active ingredients of the present invention is evident from the test results which are recorded in the following Tables.

Crop Selectivity and Weed Control of Compounds According to the Invention in Pre-emergence Application The compounds of the invention showed at crop selective doses excellent herbicidal activity. This could be particularly demonstrated by the Examples 1 and 53 which displayed complete control of all the eight weed species at the wheat selective dose of 0.1 kg/ha. Example 4 exhibited complete weed control at the wheat selective dose of 0.4 kg/ha. Furthermore, the compounds of the present invention displayed good selectivity in maize and soybeans as exemplified by Example 4 exhibiting high levels of activity on the weeds included in the test at the crop selective dose of 0.1 kg/ha. Thus, there is evidence for the good potential of the compounds of the invention for excellent cross spectrum control of both grasses and broadleaf weeds in key crops. The results of these tests are presented in Table A below.

TABLE A

| example | rate | ABUTH | GALAP | IPOHE | MATIN | STEME | ALOMY | ECHCG | SETVI | GLXMA | TRZAW | ZEAMX |
|---|---|---|---|---|---|---|---|---|---|---|---|---|
| 1 | 0.400 | 9 | 8 | 9 | 9 | 9 | 9 | 9 | 9 | 4 | 3 | 5 |
|   | 0.100 | 9 | 8 | 9 | 9 | 9 | 9 | 9 | 9 | 3 | 2 | 4 |
|   | 0.025 | 8 | 6 | 6 | 9 | 9 | 7 | 7 | 9 | 2 | 1 | 2 |
| 2 | 0.400 | 8 | 8 | 8 | 9 | 9 | 8 | 8 | 9 | 4 | 5 | 5 |
|   | 0.100 | 7 | X | 5 | 8 | 9 | 8 | 8 | 9 | 2 | 3 | 5 |
|   | 0.025 | 3 | 7 | 5 | 8 | 9 | 8 | 7 | 9 | 0 | 2 | 4 |
| 3 | 0.400 | 7 | 7 | 9 | 9 | 9 | 8 | 8 | 9 | 2 | 3 | 3 |
|   | 0.100 | 5 | 7 | 9 | 9 | 9 | 8 | 6 | 9 | 1 | 2 | 2 |
|   | 0.025 | 5 | 2 | 7 | 8 | 9 | 5 | 4 | 8 | 1 | 1 | 2 |

TABLE A-continued

| example | rate | ABUTH | GALAP | IPOHE | MATIN | STEME | ALOMY | ECHCG | SETVI | GLXMA | TRZAW | ZEAMX |
|---|---|---|---|---|---|---|---|---|---|---|---|---|
| 4 | 0.400 | 9 | 8 | 9 | 8 | 9 | 8 | 9 | 9 | 3 | 2 | 4 |
|  | 0.100 | 7 | 8 | 9 | 8 | 9 | 8 | 8 | 9 | 2 | 0 | 2 |
|  | 0.025 | 3 | 4 | 6 | 8 | 9 | 5 | 3 | 8 | 1 | 0 | 2 |
| 5 | 0.400 | 8 | 7 | 9 | 9 | 9 | 8 | 9 | 9 | 3 | 6 | 4 |
|  | 0.100 | 8 | 7 | 9 | 8 | 9 | 8 | 8 | 9 | 2 | 3 | 3 |
|  | 0.025 | 5 | 5 | 8 | 8 | 9 | 7 | 6 | 8 | 2 | 2 | 2 |
| 51 | 0.400 | 9 | 8 | 9 | 9 | 9 | 8 | 9 | 9 | 6 | 6 | 5 |
|  | 0.100 | 9 | 8 | 9 | 9 | 9 | 8 | 9 | 8 | 5 | 4 | 4 |
|  | 0.025 | 9 | 8 | 9 | 8 | 9 | 8 | 7 | 8 | 4 | 2 | 3 |
| 53 | 0.400 | 9 | 8 | 9 | 9 | 9 | 8 | 9 | 8 | 6 | 4 | 4 |
|  | 0.100 | 9 | 8 | 8 | 8 | 9 | 8 | 8 | 8 | 4 | 2 | 4 |
|  | 0.025 | 9 | 4 | 8 | 8 | 9 | 8 | 7 | 8 | 4 | 1 | 2 |

2. Post-emergence Herbicidal Evaluation of Test Compounds

The post-emergence herbicidal activity of the compounds of the present invention is demonstrated by the following test, wherein a variety of monocotyledonous and dicotyledonous plants are treated with formulations prepared from solutions of the test compounds in acetone containing 0.4% by weight of an alkylphenol/ethylene oxide condensate available under the trade mark TRITON X-1 55. These acetone solutions are diluted with water and the resulting formulations applied at dosage levels equivalent of about 0.025 to 0.4 kg per hectare of test compound per pot. After spraying the plants are placed on greenhouse benches and are cared for in the usual manner, commensurate with conventional greenhouse practices. From 3 weeks after treatment, the seedling plants are examined and rated according to the rating system provided above. A rating 0 indicates growth as untreated control, a rating 9 indicates death. The results of the test are set out in Table B below.

In post-emergence application the compounds of the invention displayed good overall levels of performance against weeds. This holds true in particular for the Example 53 with high levels of activity against weeds down to the lowest dose of 0.025 kg/ha.

What is claimed is:
1. A complex of formula IA

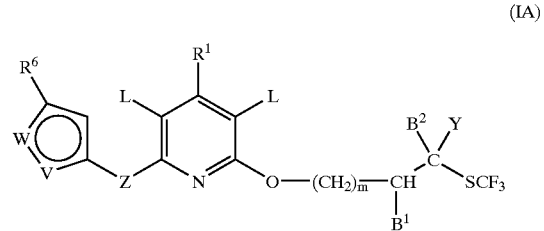

(IA)

TABLE B

| example | rate | ABUTH | GALAP | IPOHE | MATIN | STEME | ALOMY | ECHCG | LOLMU | SETVI |
|---|---|---|---|---|---|---|---|---|---|---|
| 1 | 0.400 | 6 | 8 | 9 | 8 |  | 8 | 9 |  | 8 |
|  | 0.100 | 6 | 5 | 8 | 7 |  | 7 | 9 |  | 8 |
|  | 0.025 | 5 | 2 | 8 | 5 |  | 4 | 6 |  | 5 |
|  | 0.100 |  |  |  |  |  |  |  | 8 |  |
| 2 | 0.400 | 7 | 7 | 9 | 6 | 5 | 7 | 8 |  | 8 |
|  | 0.100 | 7 | 7 | 9 | 6 | 5 | 7 | 8 |  | 8 |
|  | 0.025 | 6 | 6 | 8 | 6 | 4 | 7 | 8 |  | 7 |
|  | 0.100 |  |  |  |  |  |  |  | 8 |  |
| 3 | 0.400 | 7 | 8 | 9 | 7 | 6 | 7 | 9 |  | 9 |
|  | 0.100 | 7 | 8 | 9 | 6 | 5 | 7 | 8 |  | 9 |
|  | 0.025 | 5 | 8 | 9 | 5 | 4 | 5 | 6 |  | 8 |
|  | 0.100 |  |  |  |  |  |  |  | 8 |  |
| 4 | 0.400 | 8 | 9 | 9 | 8 | 8 | 8 | 9 |  | 9 |
|  | 0.100 | 7 | 8 | 7 | 7 | 5 | 8 | 8 |  | 7 |
|  | 0.025 | 5 | 7 | 5 | 4 | 5 | 6 | 8 |  | 5 |
|  | 0.100 |  |  |  |  |  |  |  | 8 |  |
| 5 | 0.400 | 8 | 8 | 9 | 7 | 7 | 8 | 8 |  | 9 |
|  | 0.100 | 8 | 8 | 9 | 7 | 5 | 7 | 8 |  | 9 |
|  | 0.025 | 7 | 7 | 9 | 6 | 4 | 6 | 7 |  | 9 |
|  | 0.100 |  |  |  |  |  |  |  | 8 |  |
| 51 | 0.400 | 8 | 9 | 9 | 8 | 9 | 8 | 9 |  | 9 |
|  | 0.100 | 8 | 9 | 9 | 6 | 9 | 7 | 9 |  | 9 |
|  | 0.025 | 7 | 6 | 9 | 4 | 8 | 4 | 9 |  | 8 |
|  | 0.100 |  |  |  |  |  |  |  | 8 |  |
| 53 | 0.400 | 9 | 9 | 9 | 8 | 9 | 9 | 9 |  | 9 |
|  | 0.100 | 9 | 9 | 9 | 8 | 9 | 8 | 9 |  | 9 |
|  | 0.025 | 8 | 6 | 9 | 6 | 8 | 6 | 9 |  | 9 |
|  | 0.100 |  |  |  |  |  |  |  | 8 |  | wherein
 W—V represents N—CH, S—CH, N—CH—CH
 CH—CH—CH or N—NR$^7$;
 m is 0 or 1;
 B$^1$ and B$^2$ represent a hydrogen atom or taken together a double bond;
 L represents a hydrogen or fluorine atom;
 Z represents an oxygen atom;
 R$^1$ represents a hydrogen or halogen atom or an optionally substituted alkyl, alkenyl, alkynyl, alkoxy, alkoxyalkyl, alkoxyalkoxy group or a haloalkyl, haloalkoxy, cyano, nitro or SF$_5$ group, or —S(O)$_P$—R$^2$, in which p is 0, 1 or 2, and R$^2$ represents an alkyl or haloalkyl group; or —NR$^3$R$^4$, in which R$^3$ and R$^4$ each independently represent a hydrogen atom, an alkyl, alkenyl, aralkyl or aryl group;
 R$^6$ represents a halogen atom or an optionally substituted alkyl group;
 R$^7$ represents an alkyl group; and
 Y represents a hydrogen or halogen atom.

2. A compound selected from the group consisting of
2-(1-methyl-3-trifluoromethylpyrazol-5-yloxy)-6-(3-trifluoromethylthio-propoxy)-4-methylpyridine;
2-(1-methyl-3-trifluoromethylpyrazol-5-yloxy)-6-(2-trifluoromethylthio-ethoxy)-4-methylpyridine;
2-(1-methyl-3-trifluoromethylpyrazol-5-yloxy)-6-(3-chloro-3-trifluoromethylthiopropoxy)-4-methylpyridine;
2-(5-trifluoromethylthien-3-yloxy)-6-(3-trifluoromethylthiopropoxy)-4-methylpyridine;
2-(5-trifluoromethylthien-3-yloxy)-6-(2-trifluoromethylthioethoxy)-4-methylpyridine;
2-(5-trifluoromethylthien-3-yloxy)-6-(3-chloro-3-trifluoromethylthio-propoxy)-4-methylpyridine;
2-(3-trifluoromethylphenoxy)-6-(3-trifluoromethylthiopropoxy)-4-methylpyridine;
2-(3-trifluoromethylphenoxy)-6-(2-trifluoromethylthioethoxy)-4-methylpyridine;
2-(3-trifluoromethylphenoxy)-6-(3-chloro-3-trifluoromethylthio-propoxy)-4-methylpyridine;
2-(2-difluoromethoxypyrid-4-yloxy)-6-(3-trifluoromethylthiopropoxy)-4-methylpyridine;
2-(2-difluoromethoxypyrid-4-yloxy)-6-(2-trifluoromethylthioethoxy)-4-methylpyridine;
2-(2-difluoromethoxypyrid-4-yloxy)-6-(3-chloro-3-trifluoromethylthio-propoxy)-4-methylpyridine;
2-(2-trifluoromethylpyrid-4-yloxy)-6-(3-trifluoromethylthiopropoxy)-4-methylpyridine,
2-((2-trifluoromethylpyrid-4-yloxy)-6-(2-trifluoromethylthioethoxy)-4-methylpyridine,
2-((2-trifluoromethylpyrid-4-yloxy)-6-(3-chloro-3-trifluoromethylthio-propoxy)-4-methylpyridine;
2-(1-methyl-3-trifluoromethylpyrazol-5-yloxy)-6-(3-trifluoromethylthio-prop-2-enyloxy)-4-methylpyridine;
2-(1-methyl-3-trifluoromethylpyrazol-5-yloxy)-6-(3-chloro-3-trifluoromethylthio-prop-2-enyloxy)-4-methylpyridine;
2-(5-trifluoromethylthien-3-yloxy)-6-(3-trifluoromethylthio-prop-2-enyloxy)-4-methylpyridine;
2-(5-trifluoromethylthien-3-yloxy)-6-(3-chloro-3-trifluoromethylthio-prop-2-enyloxy)-4-methylpyridine;
2-(3-trifluoromethylphenoxy)-6-(3-trifluoromethylthio-prop-2-enyloxy)-4-methylpyridine;
2-(3-trifluoromethylphenoxy)-6-(3-chloro-3-trifluoromethylthio-prop-2-enyloxy)-4-methylpyridine;
2-(2-difluoromethoxypyrid-4-yloxy)-6-(3-trifluoromethylthio-prop-2-enyloxy)-4-methylpyridine;
2-(2-difluoromethoxypyrid-4-yloxy)-6-(3-chloro-3-trifluoromethylthio-prop-2-enyloxy)-4-methylpyridine;
2-(2-trifluoromethylpyrid-4-yloxy)-6-(3-trifluoromethylthio-prop-2-enyloxy)-4-methylpyridine;
2-(2-trifluoromethylpyrid-4-yloxy)-6-(3-chloro-3-trifluoromethylthio-prop-2-enyloxy)-4-methylpyridine;
2-(1-methyl-3-trifluoromethylpyrazol-5-yloxy)-6-(3-trifluoromethylthio-propyloxy)-pyridine;
2-(1-methyl-3-trifluoromethylpyrazol-5-yloxy)-6-(2-trifluoromethylthio-ethoxy)-pyridine;
2-(1-methyl-3-trifluoromethylpyrazol-5-yloxy)-6-(3-trifluoromethylthio-propyloxy)-4-cyanopyridine;
2-(1-methyl-3-trifluoromethylpyrazol-5-yloxy)-6-(2-trifluoromethylthio-ethoxy)-4-cyanopyridine;
2-(1-methyl-3-trifluoromethylpyrazol-5-yloxy)-6-(3-trifluoromethylthio-propyloxy)-4-methoxypyridine;
2-(1-methyl-3-trifluoromethylpyrazol-5-yloxy)-6-(2-trifluoromethylthio-ethoxy)-4-methoxypyridine;
2-(3-trifluoromethylphenoxy)-6-(3-trifluoromethylthio-propyloxy)-4-cyanopyridine;
2-(3-trifluoromethylphenoxy)-6-(2-trifluoromethylthio-ethoxy)-4-cyanopyridine;
2-(3-trifuoromethylphenoxy)-6-(3-trifluoromethylthio-propyloxy)-4-methoxypyridine;
2-(3-trifluoromethylphenoxy)-6-(2-trifluoromethylthio-ethoxy)-4-methoxypyridine;
2-(2-difluoromethoxypyrid-4-yloxy)-6-(3-trifluoromethylthio-propyloxy)-pyridine;
2-(2-difluoromethoxypyrid-4-yloxy)-6-(2-trifluoromethylthio-ethoxy)-pyridine;
2-(2-difluoromethoxypyrid-4-yloxy)-6-(3-trifluoromethylthio-propyloxy)-4-cyanopyridine;
2-(2-difluoromethoxypyrid-4-yloxy)-6-(2-trifluoromethylthio-ethoxy)-4-cyanopyridine;
2-(2-difluoromethoxypyrid-4-yloxy)-6-(3-trifluoromethylthio-propyloxy)-4-methoxypyridine;
2-(2-difluoromethoxypyrid-4-yloxy)-6-(2-trifuoromethylthio-ethoxy)-4-methoxypyridine;
2-(2-trifluoromethylpyrid-4-yloxy)-6-(3-trifluoromethylthio-propyloxy)-pyridine;
2-(2-trifluoromethylpyrid-4-yloxy)-6-(2-trifluoromethylthio-ethoxy)-pyridine;
2-(2-trifuoromethylpyrid-4-yloxy)-6-(3-trifluoromethylthio-propyloxy)-4-cyanopyridine;
2-(2-trifluoromethylpyrid-4-yloxy)-6-(2-trifluoromethylthio-ethoxy)-4-cyanopyridine;
2-(2-trifluoromethylpyrid-4-yloxy)-6-(3-trifluoromethylthio-propyloxy)-4-methoxypyridine;
2-(2-trifluoromethylpyrid-4-yloxy)-6-(2-trifluoromethylthio-ethoxy)-4-methoxypyridine.

3. A herbicidal composition comprising a herbicidally effective amount of at least one compound of formula IA, as claimed in claim 1, together with a carrier.

4. A composition as claimed in claim 3, comprising at least two carriers, at least one of which is a surface-active agent.

5. A method of combating undesired plant growth at a locus, comprising application to the locus of an effective amount of at least one compound of formula IA, as claimed in claim 1.

6. A process for the preparation of a compound as claimed in claim 1, which comprises reacting a respective compound of the following formula,

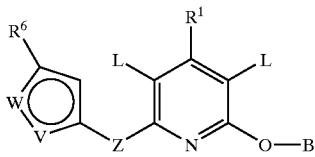
in which B represents a hydrogen atom or a group of the following formula
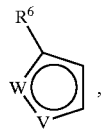
with a compound of the following formula
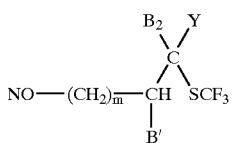
or a metal salt thereof.
* * * * *

UNITED STATES PATENT AND TRADEMARK OFFICE
CERTIFICATE OF CORRECTION

PATENT NO. : 6,534,447 B1
DATED : March 18, 2003
INVENTOR(S) : Scheiblich et al.

It is certified that error appears in the above-identified patent and that said Letters Patent is hereby corrected as shown below:

Column 22,
Line 25, "(3-trifuoromethylphenoxy)" should be -- (3-trifluoromethylphenoxy) --.

Signed and Sealed this

Twenty-fourth Day of June, 2003

JAMES E. ROGAN
*Director of the United States Patent and Trademark Office*